US009585687B2

(12) United States Patent
Tenenbaum et al.

(10) Patent No.: US 9,585,687 B2
(45) Date of Patent: Mar. 7, 2017

(54) METHOD AND APPARATUS FOR COSMETIC SKIN CARE

(75) Inventors: Fabian Tenenbaum, Tenafly, NJ (US); Lion Flyash, Nazareth Illit (IL); Shimon Eckhouse, Haifa (IL)

(73) Assignee: SYNERON MEDICAL LTD., Yoqneam Illit (IL)

( * ) Notice: Subject to any disclaimer, the term of this patent is extended or adjusted under 35 U.S.C. 154(b) by 372 days.

(21) Appl. No.: 14/237,356

(22) PCT Filed: Aug. 2, 2012

(86) PCT No.: PCT/IL2012/000298
§ 371 (c)(1), (2), (4) Date: Apr. 15, 2014

(87) PCT Pub. No.: WO2013/021380
PCT Pub. Date: Feb. 14, 2013

(65) Prior Publication Data

US 2014/0222026 A1 Aug. 7, 2014

Related U.S. Application Data

(60) Provisional application No. 61/521,538, filed on Aug. 9, 2011.

(51) Int. Cl.
*A61B 17/3205* (2006.01)
*A61B 18/20* (2006.01)
(Continued)

(52) U.S. Cl.
CPC ........ *A61B 17/3205* (2013.01); *A61B 18/203* (2013.01); *A61N 1/0476* (2013.01);
(Continued)

(58) Field of Classification Search
CPC ............. A61B 17/3205; A61B 18/203; A61B 2017/320012; A61B 2018/00452;
(Continued)

(56) References Cited

U.S. PATENT DOCUMENTS 4,398,113 A 8/1983 Lewis et al.
2004/0009141 A1 1/2004 Koenig et al.
(Continued)

FOREIGN PATENT DOCUMENTS

WO 2009104179 A2 8/2009

OTHER PUBLICATIONS

PCT Search Report & Written Opinion in PCT/IL2012/000298, dated Dec. 17, 2012.

*Primary Examiner* — Quang D Thanh
(74) *Attorney, Agent, or Firm* — Manelli Selter PLLC; Edward J. Stemberger

(57) ABSTRACT

The present method and apparatus seek to provide cosmetic skin care including application in concert or consecutively of various types of energy to bring about a welcomed combination of skin cleansing and skin rejuvenation and enhancing. There is thus provided, in accordance with an exemplary embodiment of the current method and apparatus an apparatus for cosmetic skin care including a brush-like head having a multiplicity of bristles attached to one or more carriers at least a portion of which is operative to apply forms of energy to the skin. At least one of the forms of energy is RF energy while other forms include light energy, mechanical energy, ultrasound energy and any suitable combination thereof.

26 Claims, 12 Drawing Sheets

234 202 238 206 216 230 232 212 212 X X 216 208 208 236 202 216 106 114 212 d 212

SECTION X-X

(51) Int. Cl.

| | |
|---|---|
| ***A61N 5/01*** | (2006.01) |
| ***A61N 5/06*** | (2006.01) |
| ***A61N 1/32*** | (2006.01) |
| ***A61N 1/04*** | (2006.01) |
| *A61B 18/00* | (2006.01) |
| *A61B 17/32* | (2006.01) |

(52) U.S. Cl.

CPC ............... *A61N 1/328* (2013.01); *A61N 5/01* (2013.01); *A61N 5/0616* (2013.01); *A61B 2017/320012* (2013.01); *A61B 2018/0047* (2013.01); *A61B 2018/00452* (2013.01); *A61B 2018/202* (2013.01)

(58) Field of Classification Search

CPC ...... A61B 2018/202; A61B 2018/0047; A61N 1/0476; A61N 1/328; A61N 5/0616; A61N 5/01; A61H 7/00; A61H 7/002; A61H 7/003; A61H 7/004; A61H 7/005; A61H 7/007; A61H 23/00; A61H 23/02; A61H 23/0245; A61H 23/06; A61H 2201/0153; A61H 2201/0157; A61H 2201/0221; A61H 2201/10; A61H 2201/12; A61H 2201/1207; A61H 2201/02; A61H 2201/0207

See application file for complete search history.

(56) References Cited

U.S. PATENT DOCUMENTS

| | | | | |
|---|---|---|---|---|
| 2005/0159741 | A1 | 7/2005 | Paul et al. | |
| 2005/0277950 | A1* | 12/2005 | Pilcher .................. | A61B 17/54 606/131 |
| 2007/0179490 | A1 | 8/2007 | Azar et al. | |
| 2008/0172112 | A1* | 7/2008 | Gourgouliatos ..... | A61N 5/0617 607/89 |
| 2009/0177125 | A1* | 7/2009 | Pilcher .............. | A46B 15/0034 601/18 |
| 2010/0016727 | A1 | 1/2010 | Rosenberg | |
| 2011/0184499 | A1* | 7/2011 | Radi ..................... | A61H 7/005 607/88 |

* cited by examiner

METHOD AND APPARATUS FOR COSMETIC SKIN CARE

TECHNICAL FIELD

The current method and apparatus relate to the field of personal cosmetic care procedures and in particular cosmetic skin care procedures.

BACKGROUND

Facial skin is one of the most common skin areas cosmetically attended to. Traditional cosmetic facial skin care involves facial skin massage and skin exfoliation employing cleansing tools such as woven mesh sponges. Such cleansing tools tend to be too harsh for the skin on the face and may cause increased dryness and irritation.

Facial cloths are used to remove dirt, oil and makeup but leave skin debris and clogged pores on the face, leading to facial irritation such as pimples or blackheads.

The practice of using heat energy for cosmetic skin treatment is known. Heating the skin and underlying tissues causes tissue shrinkage and produces the desired cosmetic effect.

The use of RF energy emitting devices for cosmetic skin treatment is also known. Cosmetic RF skin treatment is administered using an applicator coupled with one or more RF electrodes. The electrodes RF energy delivery surface, coupled with the surface of the skin, generate in the skin an electric current that heats the skin and underlying subcutaneous tissues to create the desired effect of tissue shrinkage.

The use of light energy in the form of visible light, infra-red (IR) light or coherent light in cosmetic skin treatment is also used in cosmetic skin treatment. Cosmetic Lasers and LED Light Therapy have shown to contribute to skin rejuvenation and reverse and control the visible signs of aging. Both visible and infrared light have been shown to effect various positive changes at a cellular level.

The application in concert of RF energy, light energy and mechanical massage energy in cosmetic skin care bring about a welcomed combination of skin cleansing and skin rejuvenation, enhancing the appearance of treated facial skin. Such apparatuses however exist for professional use only and the treatment is performed in cosmetic clinics under supervision of qualified personnel.

Recently, the at-home use of personal cosmetic skin care and skin cleansing devices have become popular. The present apparatus and method provide a solution for conducting a cosmetic skin care cleansing in residential conditions by a casual apparatus user. The treatment could result in similar or close to similar cosmetic skin cleansing results, as treatment performed in cosmetic clinic results.

SUMMARY

The present method and apparatus seek to provide cosmetic skin care including application in concert or consecutively of various types of energy to bring about a welcomed combination of skin cleansing and skin rejuvenation and enhancing There is thus provided, in accordance with an exemplary embodiment of the current method and apparatus an apparatus for cosmetic skin care including a brush-like head having a multiplicity of bristles attached to one or more carriers at least a portion of which is operative to apply forms of energy to the skin. At least one of the forms of energy is RF energy while other forms include light energy, mechanical energy, ultrasound energy and any suitable combination thereof.

In accordance with another exemplary embodiment of the present method and apparatus, there is also provided a brush-like head that may be attached to a handle and having a multiplicity of bristles attached to one or more carriers at least a portion of which is operative to apply forms of energy to the skin and also including LEDs to directly or indirectly apply light energy to the skin.

In accordance with yet another exemplary embodiment of the present method and apparatus, the brush-like head may also include one or more soft pads lined with a material easily charged with a stationary electrical charge.

In accordance with still another exemplary embodiment of the present method and apparatus, the brush-like head carrier may also include one or more stationary portions and at one or more rotatably moveable portions.

In accordance with another exemplary embodiment of the present method and apparatus, the RF energy applying bristles may be arranged in a monopolar or bipolar configuration.

In accordance with yet another exemplary embodiment of the present method and apparatus, the RF energy applying bristles may also include a grounding electrode located on the handle or on the brush-like head.

In accordance with still another exemplary embodiment of the present method and apparatus, the carrier may be translational in one or more directions and include a rail, wheel and motor mechanism, a rail, wheel and electromagnet mechanism, a rotational mechanism or a piezoelectric mechanism.

In accordance with another exemplary embodiment of the present method and apparatus, there is also provided a gel reservoir in or attached to the brush-like head and operative to hold and apply electric-conductive cleansing gel through pores in the brush-like head carrier.

In accordance with yet another exemplary embodiment of the present method and apparatus, there is also provided a method for cosmetic skin care including brushing skin with a brush-like head having a multiplicity of bristles attached to a carrier, operative to apply forms of energy to the skin, applying at one or more forms of energy of which at least one form is RF energy to the skin and in which another form of energy may be vibrating mechanical energy to massage and exfoliate said skin.

BRIEF DESCRIPTION OF THE DRAWINGS

The present apparatus and method will be understood and appreciated more fully from the following detailed description, taken in conjunction with the drawings in which.

DETAILED DESCRIPTION

Figure 1:
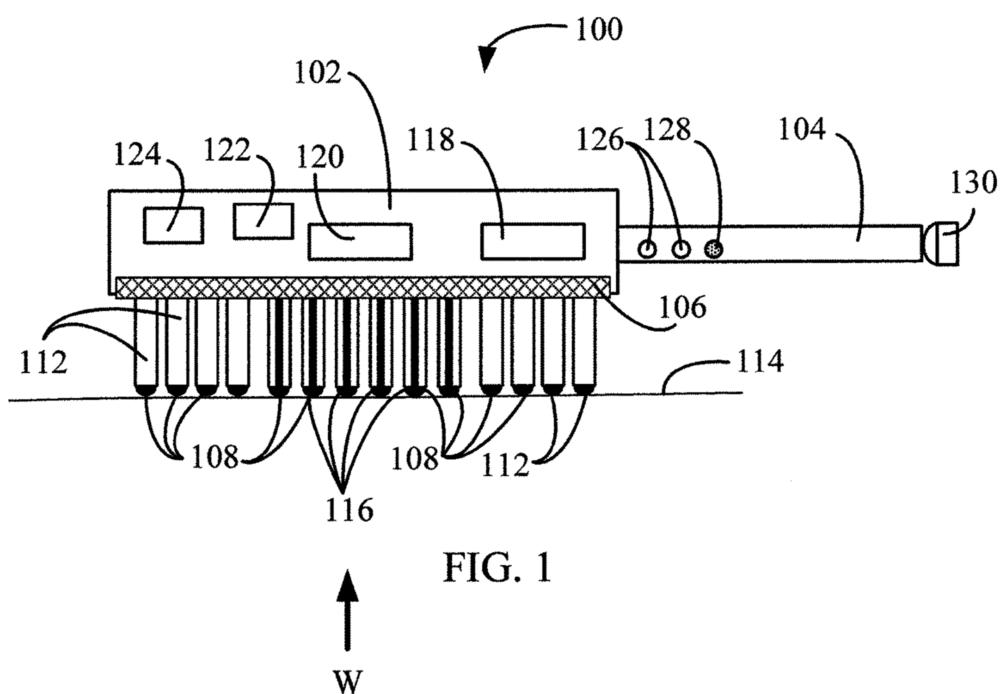
FIG. 1 is a cross-section view simplified illustration of an exemplary embodiment in accordance with the current method and apparatus.

Reference is made to FIG. 1, which is a cross-section view simplified illustration of an exemplary embodiment in accordance with the current method and apparatus. An apparatus for cosmetic skin care or cleansing 100 includes a head 102 which may be brush-like in appearance and may include one or more carriers 106 and a multiplicity of semi-rigid or pliable bristles 108 attached to carrier 106. A portion of bristles 108 may be regular brush bristles made of any pliable material such as plastic, rubber and others.

At least one portion of bristles 108 may include RF energy applying bristles 112 operative to apply RF energy to skin 114 in contact with bristles 108. Additionally or alternatively, at least one portion of bristles 108 may be light delivering bristles 116 operative to apply light energy to skin 114.

In some embodiments, apparatus 100 could include a handle 104. The handle may be designed to be comfortable to hold when manipulating and translating head 102 over skin 114.

Head 102 and/or handle 104 could include components such as a power source 118 and different sources of energy. For example, an RF generator 120, a light source 122, a controller 124 and indicator lights 126. Power source 118 may be rechargeable. Handle 104 may also include an On/Off switch 128 and a plug or socket 130 for connecting rechargeable power source 118 to a charger (not shown).

Figure 2:
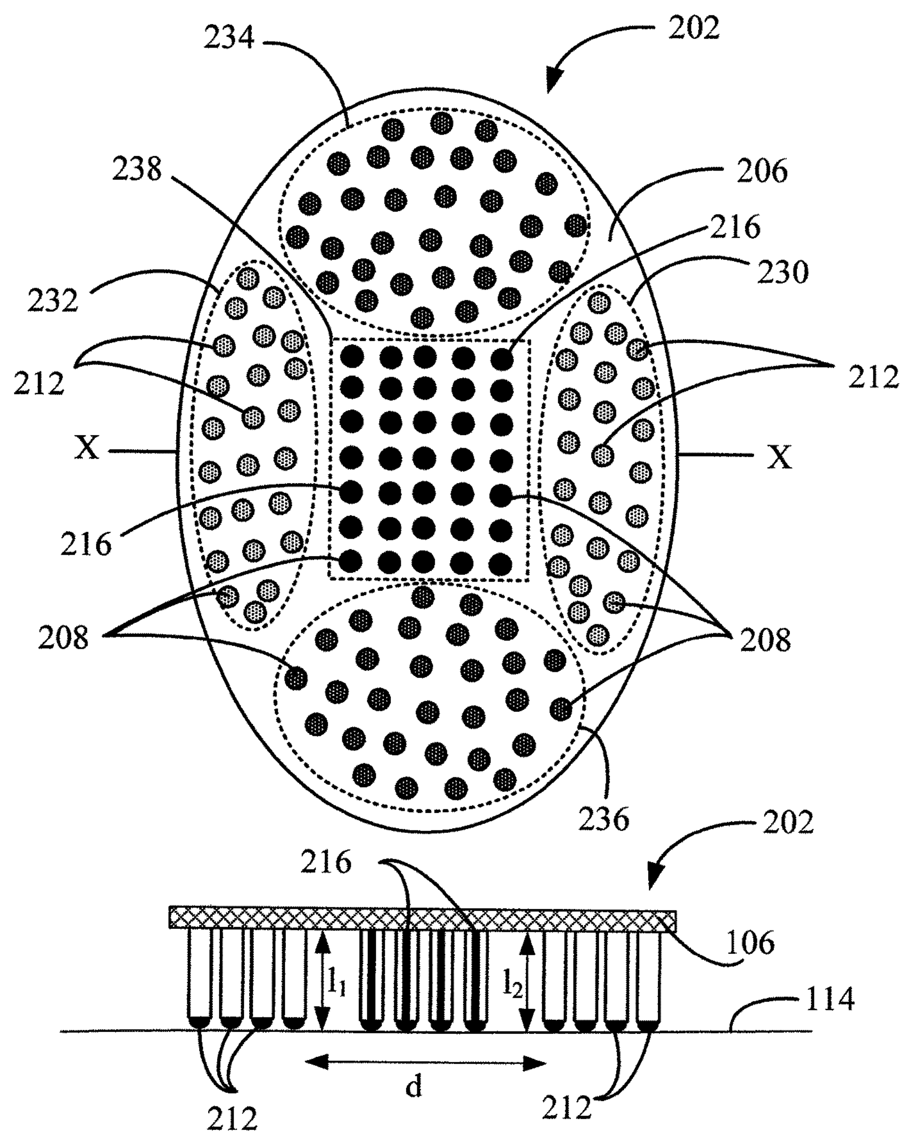
FIG. 2 is a plan view and cross-section view simplified illustration of another exemplary embodiment in accordance with the current method and apparatus.

Referring now to FIG. 2, which is a plan view and cross-section view simplified illustration of head 202, similar to head 102 of FIG. 1 as viewed in the direction of arrow (W), of an exemplary embodiment in accordance with the current method and apparatus. Head 202 includes a combination of bristles 208 attached to carrier 206 and arranged in clusters each including a multiplicity of bristles 208 of the same type. The location of each cluster on carrier 206 may vary.

For example purposes only, clusters 230 and 232 may include RF energy applying bristles 212, clusters 234 and 236 may include regular inert brush bristles made of any pliable material such as plastic, rubber and cluster 238 may include light delivering bristles 216. RF energy applying bristles 212 may be supplied by RF generator 120 (FIG. 1) and light delivering bristles 216 may be supplied by light source 122 (FIG. 1). The shortest distance (d) between RF energy applying bristles 212 in clusters 230 and 232 closest to each other may be more than the combined lengths (l) of the bristles 212 (i.e., $d>l_1+l_2$) to avoid shorting of RF energy applying bristles 212.

Reference is now made to FIGS. 3A, 3B, 3C and 3D, which are cross-section view simplified illustrations of exemplary embodiments of light delivering bristles 316, similar to bristles 116 (FIGS. 1) and 216 (FIG. 2) in accordance with the current method and apparatus.

Figure 3A:
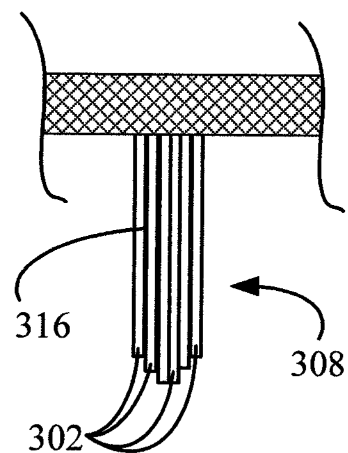
FIGS. 3A, 3B, 3C and 3D are cross-section view simplified illustrations of exemplary embodiments of light delivering bristles in accordance with the current method and apparatus.

As shown in FIG. 3A, light delivering bristles 316 may include a single optical fiber or a multiplicity of optical fibers 302 bunched together to form a bristles 308. Optical fibers 302 may be adhered to each other employing a flexible adhesive or a sleeve allowing some longitudinal relative movement between fibers 302 so that to allow a certain degree of pliability to light delivering bristles 316.

Figure 3B:
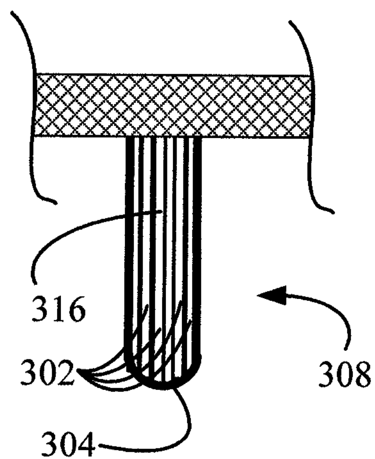

Alternatively and optionally, and as shown in FIG. 3B, light delivering bristles 316 optical fibers 302 may be coated with a pliable coating 304 so that to both maintain a certain degree of pliability to light delivering bristles 316 as well as allow passage of light to skin 114 (FIG. 1).

Figure 3C:
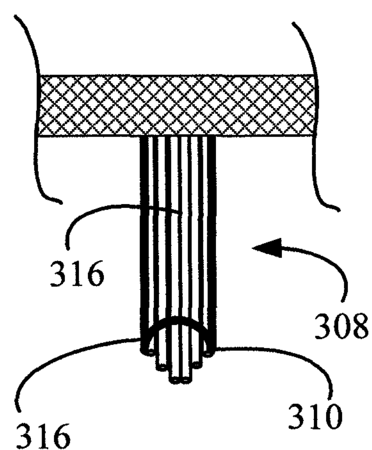

Alternatively and optionally, and as shown in FIG. 3C, light delivering bristles 316 optical fibers 302 may be enclosed within a protective sleeve 306. Sleeve 306 may be made of any type of elastic, pliable material such as plastic, rubber and similar. Optical fibers 302 may end at a rim 310 of sleeve 306 or, alternatively, protrude beyond rim 310 in which case fibers 302 may be partially coated as described hereinabove.

Figure 3D:
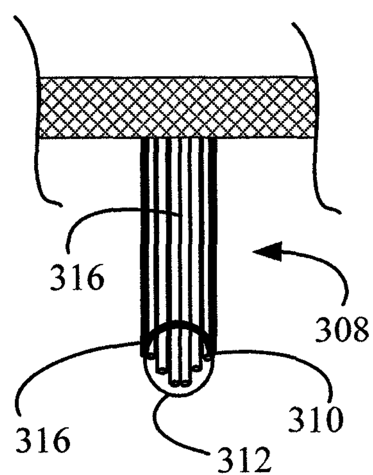

Alternatively and optionally, and as shown in FIG. 3D, a protective transparent cover 312, which may be dome-shaped or have other shape preventing accidental damage to the treated skin, may be attached to rim 310 protecting optical fibers 302 ending at, or protruding beyond rim 310 of sleeve 306.

Optical fibers may be supplied by light source 122 (FIG. 1) and may apply light energy in the form of visible light or Infra-Red (IR) light. The applied light may be in a form of a continuous, semi-continuous or pulsed form and have a wavelength of 400 nm-2000 nm. Light source 122 may be independently controlled by a dedicated switch (not shown) on handle 104, or, additionally or alternatively, be controlled by controller 124 (FIG. 1) in accordance with a predetermined protocol. The protocol could include different options of light to fibers 302 supply. For example, light may be supplied to one fiber, to a group of fibers or to all fibers 302 simultaneously.

Figure 4A:
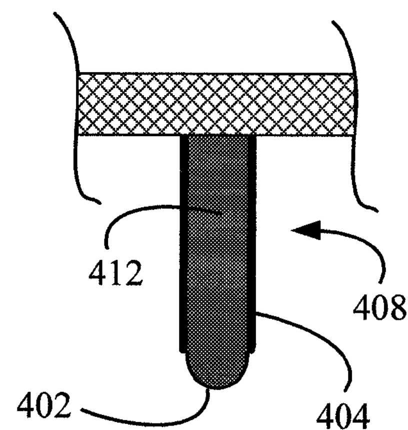
FIGS. 4A and 4B are cross-section view simplified illustrations of exemplary embodiments of RF energy applying bristles in accordance with the current method and apparatus.
Figure 4B:
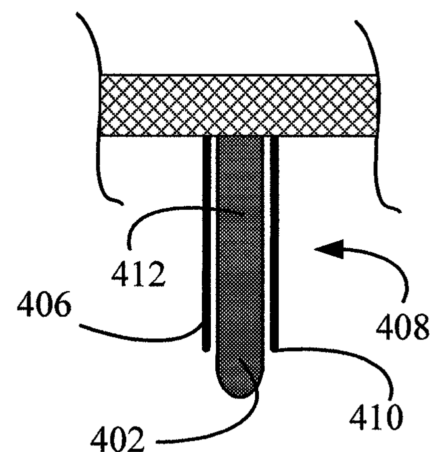

Referring now to FIGS. 4A and 4B, which are cross-section view simplified illustrations of exemplary embodiments of RF energy applying bristles 412, similar to bristles 112 (FIGS. 1) and 212 (FIG. 2) in accordance with the current method and apparatus.

As shown in FIG. 4A, Bristles 408 may include RF energy applying bristles 412 having one or more RF electrodes 402 communicating with and supplied by RF generator 120 (FIG. 1). RF energy applying bristles 412 may be partially electrically isolated by a coating or a sleeve 404.

Alternatively and optionally, and as shown in FIG. 4B, RF energy applying bristles 412 may include one or more RF electrodes 402 enclosed within a protective sleeve 406. Sleeve 406 may be made of any type of electrically isolating pliable material such as plastic, rubber and similar. RF electrodes 402 may protrude beyond rim 410.

Electrodes 402 may be made of a pliable conducting material to allow pliability to bristles 408.

Figure 5:
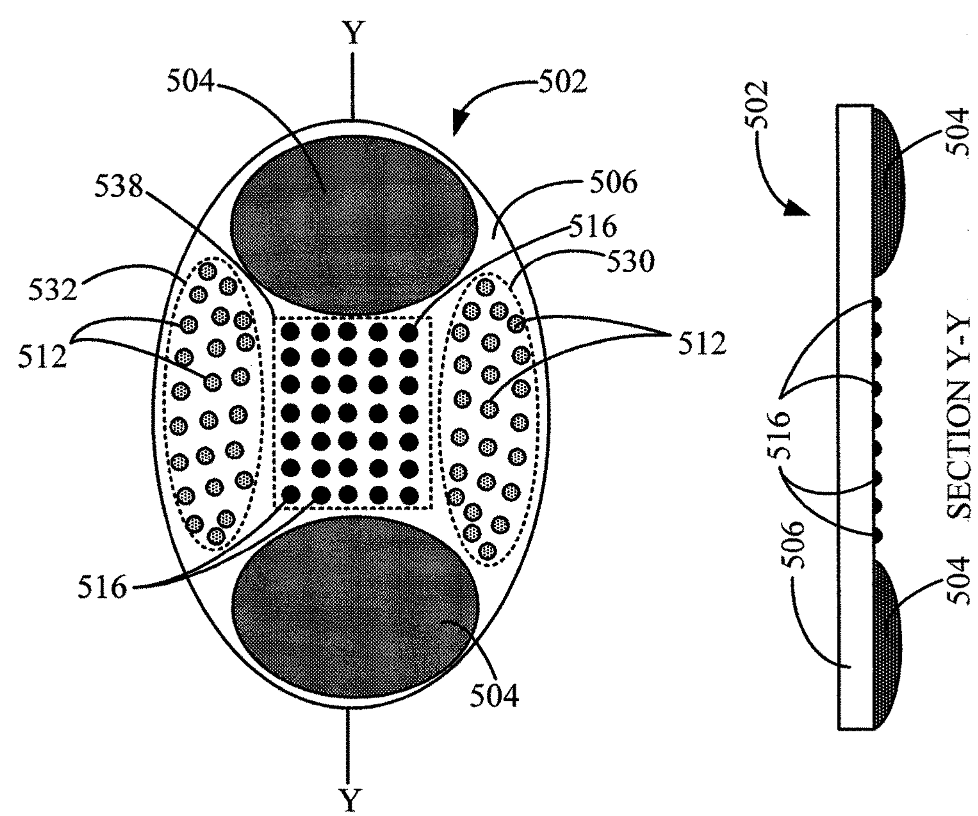
FIG. 5, which is a plan view and cross-section view simplified illustration of yet another exemplary embodiment in accordance with the current method and apparatus.

Referring now to FIG. 5, which is a plan view and cross-section view simplified illustration of head 502, similar to head 102 of FIG. 1 as viewed in the direction of arrow (W), of another exemplary embodiment in accordance with the current method and apparatus.

In FIG. 5, light delivering bristles 516 may be one or more LEDs attached to carrier 506 within cluster 538. Additionally and optionally, head 502 may also include RF energy applying bristles 512 in one or more clusters 530 and 532. Additionally and optionally, head 502 may also include one or more soft pads 504 lined with a material easily charged, for example by friction, with a stationary electrical charge such as, but not limited to, polyester, silk, styrene, and others. Pads 504 may collect loose electrically charged skin debris during and following a cosmetic skin care session. Pads 504 could be implemented as disposable and replaceable pads.

Figure 6:
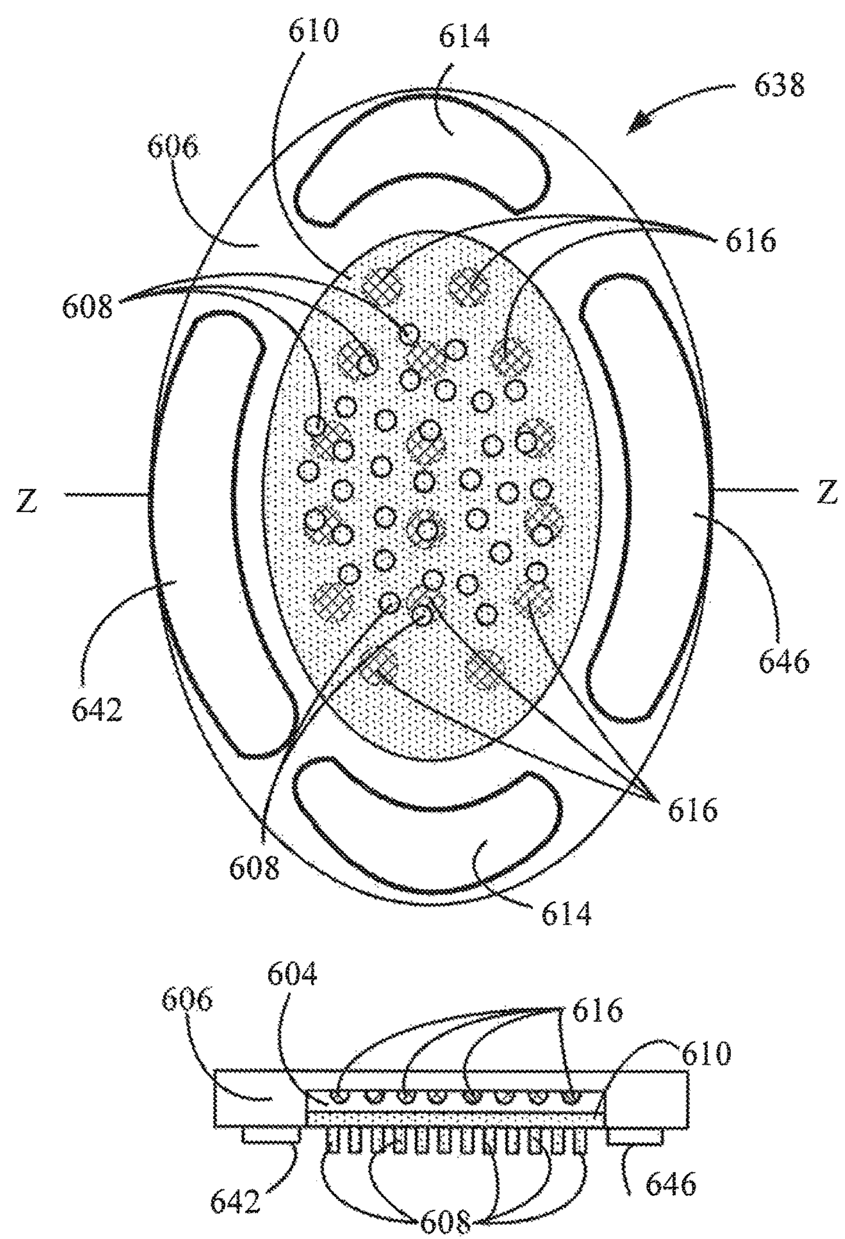
FIG. 6 is a plan view and cross-section views simplified illustration of still another exemplary embodiment in accordance with the current method and apparatus.

As shown in FIG. 6, which is a plan view and cross-section view simplified illustration of head 602, similar to head 102 of FIG. 1 as viewed in the direction of arrow (W), of yet another exemplary embodiment in accordance with the current method and apparatus, light delivering bristles 616 may be one or more LEDs embedded within a recess 604 within carrier 606. Regular brush bristles 608 made of any clear pliable material such as plastic, nylon or similar, may be attached to a clear plate 610 made of a clear material such as plastic, Poly(methyl methacrylate) (Plexiglas®) or similar attached to carrier 606 and covering recess 604 forming a transparent window.

Additionally and optionally, similar to head 502 (FIG. 5), head 602 may also include RF energy applying bristles 612 in one or more clusters 630 and 632 and one or more soft pads 614 for collecting electrically charged debris during and following a cosmetic skin care session.

FIG. 6, which is a plan view and cross-section view simplified illustration of head 638, similar to head 102 of FIG. 1 as viewed in the direction of arrow (W), of yet another exemplary embodiment in accordance with the current method and apparatus. RF energy applying bristles 612 in one or more clusters 630 and 632 have been replaced by solid or flexible regular electrodes 642 and 646.

In FIG. 6, light delivering bristles 616 may be one or more LEDs directly illuminating the skin (not shown) in concert or consecutively to RF energy applying elements 608.

Figure 7A:
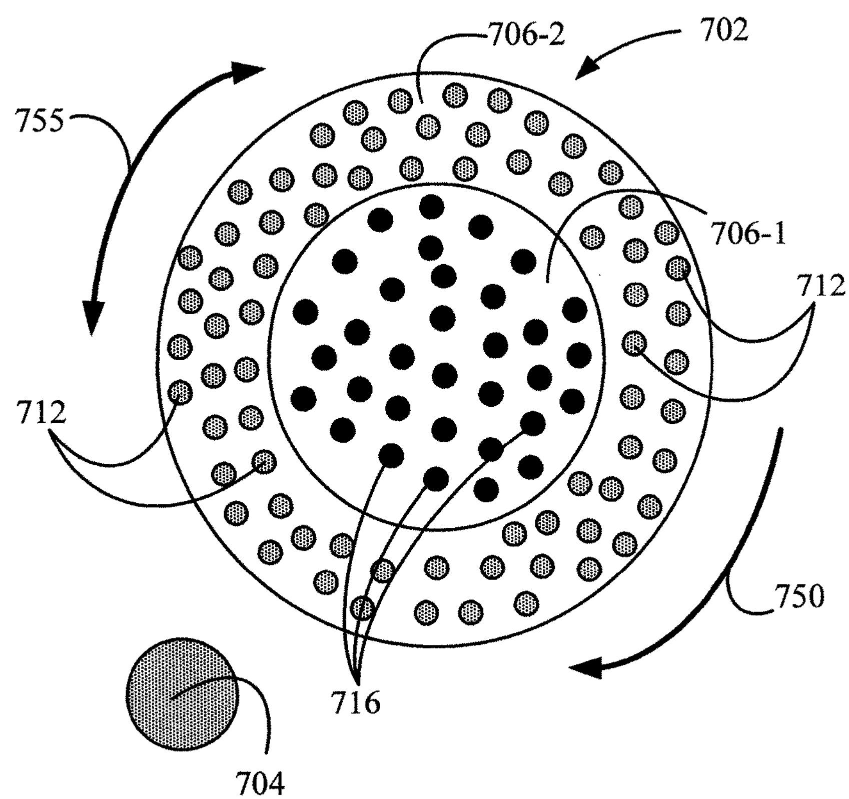
FIGS. 7A and 7B are plan view simplified illustration of two other exemplary embodiment in accordance with the current method and apparatus.
Figure 7B:
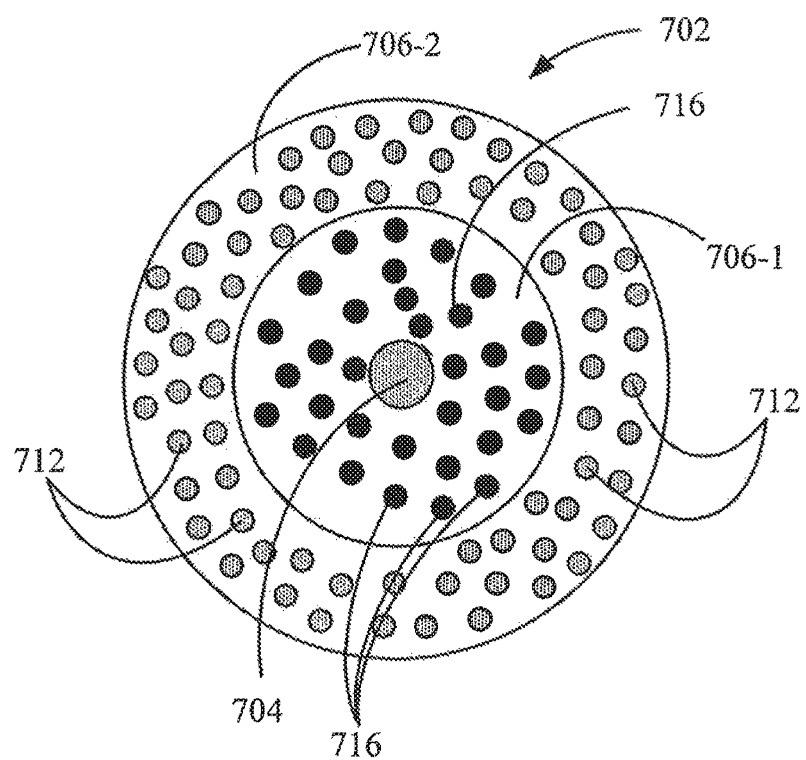

Reference is now made to FIGS. 7A and 7B, which are plan view simplified illustrations of head 702, similar to head 102 of FIG. 1 as viewed in the direction of arrow (W), of still another exemplary embodiment in accordance with the current method and apparatus. As shown in FIG. 7A, head 702 includes a carrier 706 having a stationary portion 706-1 and a rotatably moveable portion 706-2 connected to a driving electrical motor (not shown) controlled by controller 124 (FIG. 1) and powered by energy source 118 (FIG. 1).

Stationary portion 706-1 of carrier 706 may include light delivering bristles 716 in a form of optical fibers 302 bristles 308 (FIG. 3), LEDs 516 (FIG. 5) or LEDs 616 in the configuration depicted in FIG. 6.

Moveable portion 706-2 may include RF energy applying bristles 712 connected via a slip ring assembly or brush assembly (not shown) to RF generator 120 (FIG. 1). RF energy applying bristles 712 may be in a monopolar configuration to prevent shorting of bristles 712 electrodes. A common electrode 704 may be located on handle 104 (FIG. 1) in contact with the hand of an operator during operation. With proper spacing the bristles may be operated in a bi-polar configuration also.

Moveable portion 706-2 may fully rotate around stationary portion 706-1 as indicated by arrow 750 or move back and forth as indicated by arrow 755.

Movement of moveable portion 706-2 may have a massaging and exfoliating (micro abrasive) effect on skin to which head 702 is applied.

FIG. 7B depicts another configuration of the embodiment of FIG. 7B. In this configuration, grounding electrode 704 is in the center of stationary portion 706-1 of carrier 706. The shortest distance (d) between RF energy applying bristles 712 and grounding electrode 704 may be more than the length (l) of the bristles 712 (i.e., d>l) to avoid shorting of RE energy applying bristles 712.

Figure 8:
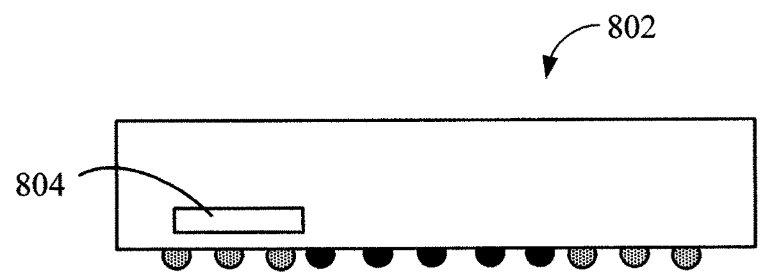
FIG. 8 is a cross-section view simplified illustration of another exemplary embodiment in accordance with the current method and apparatus.

Referring now to FIG. 8, which is a cross-section view simplified illustration of another exemplary embodiment in accordance with the current method and apparatus. Head 802 includes a vibration motor 804 supplied by energy source 118 (FIG. 1) and applying vibrating mechanical energy to head 802. Vibration motor 804 may be any type of miniature vibration motor such as a bar vibration motor, a coin vibration motor or similar and may be individually controlled by a dedicated switch on handle 104 (FIG. 1) or, additionally or alternatively, by controller 124. Vibration motor 804 effects a massaging and exfoliating effect on skin to which head 802 is applied.

Figure 9A:
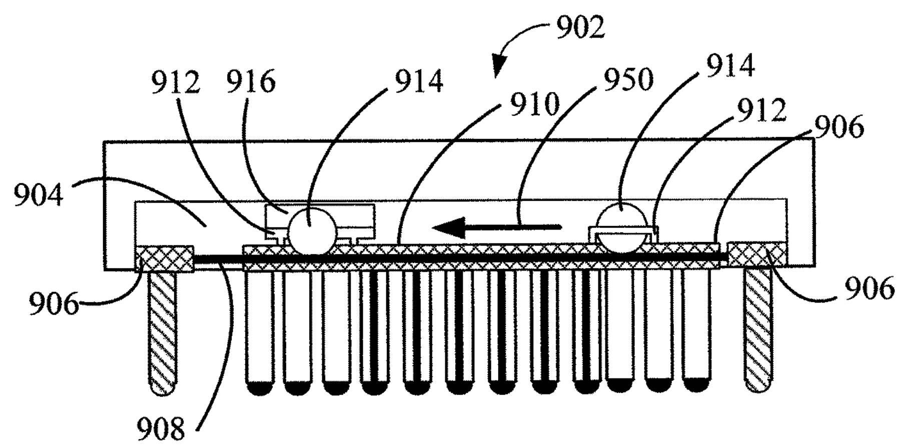
FIGS. 9A, 9B and 9C are cross-section view simplified illustrations of yet other exemplary embodiments in accordance with the current method and apparatus.
Figure 9B:
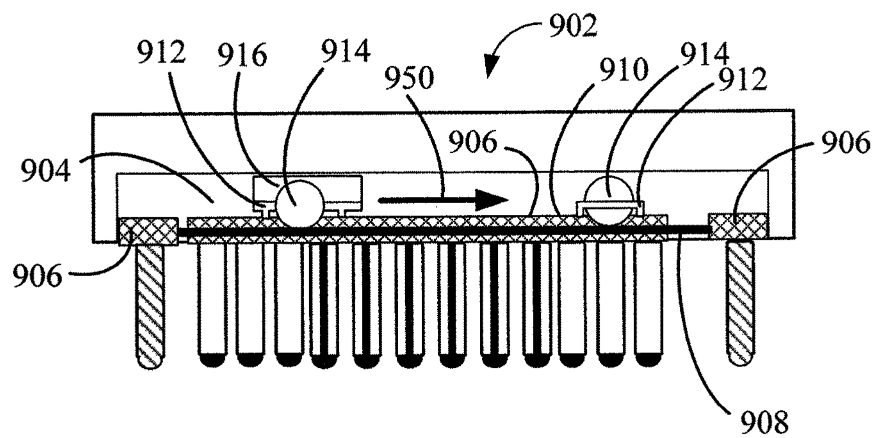

In FIGS. 9A and 9B, which are cross-section view simplified illustrations of other exemplary embodiments in accordance with the current method and apparatus, head 902 may include a recess 904 including at least one rail 908 on at least one wall of recess 904. A moveable portion 910 of carrier 906 of head 902 may be suspended from a chassis 912 having at least one wheel 914 operative to rotate along rails 908 and activated by an electric motor 916 electrically supplied by energy source 118.

Motor 916 may be individually activated by a dedicated switch (not shown) on handle 104 (FIG. 1) and controlled by controller 124. When activated, carrier 906 is translated from a first resting position, as shown in FIG. 9A, to a second resting position shown in FIG. 9B.

Motor 916 may translate carrier 906 back and forth, as indicated by arrows 950, between the resting positions indicated in FIGS. 9A and 9B. Translation of carrier 906 may have a massaging and exfoliating effect on skin to which head 902 is applied.

Alternatively and optionally one or more piezo electric elements could be incorporated into head 902 to vibrate or translate carrier 906. Vibration of carrier 906 could be performed at frequencies much higher than translation, for example, the vibration frequencies may be in ultrasonic frequency range.

Figure 9C:
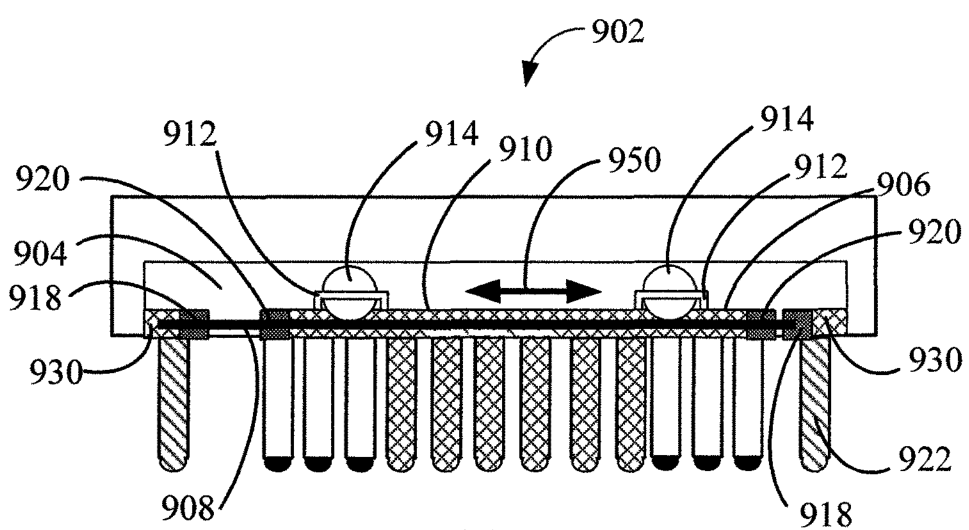

Alternatively and optionally, as shown in FIG. 9C, stationary portion 930 of carrier 906 may include at least one electromagnet 918 having an alternating polarity and moveable portion 910 may include magnets 920 located opposite to electromagnet 918. Alternating the polarity of electromagnet 918 may bring moveable portion 910 to translate back and forth, as indicated by arrow 950, along rail 908 as described hereinabove.

The distribution configuration of the various types of energy applying bristles 922 (i.e., RF applying, light applying, and other types of energy applying bristles 922, as well as regular inert bristles) may, for example purposes only, consist of moveable portion 910 including RF energy applying bristles in one of configurations similar to the configurations of FIG. 7A and inert bristles and stationary portion 930 including light applying bristles. Alternatively, another configuration may consist of moveable portion 910 including inert bristles and LEDs and stationary portion 930 including RF energy applying bristles in a monopolar or bipolar configuration. Other configurations may consist of similar or other combinations of energy applying bristles, pads charged with a stationary electrical charge and similar.

It will be appreciated by persons skilled in the art that the energy forms (i.e., RF energy, light energy, mechanical/vibration energy, ultrasound energy or any other form of applicable energy) brought forth in this disclosure may be applied concurrently, consecutively or in any other desired order of application. Additionally or alternatively, the energy forms brought forth in this disclosure may be applied in one or more modes consisting of continuous, semi-continuous or pulsed mode.

Cosmetic facial skin care commonly involves application of moisturizers, cleansers, antioxidants, clearing washes and similar. Additionally, RF skin treatment often involves the use of electric-conducting gels to improve electrode-skin contact.

Figure 10:
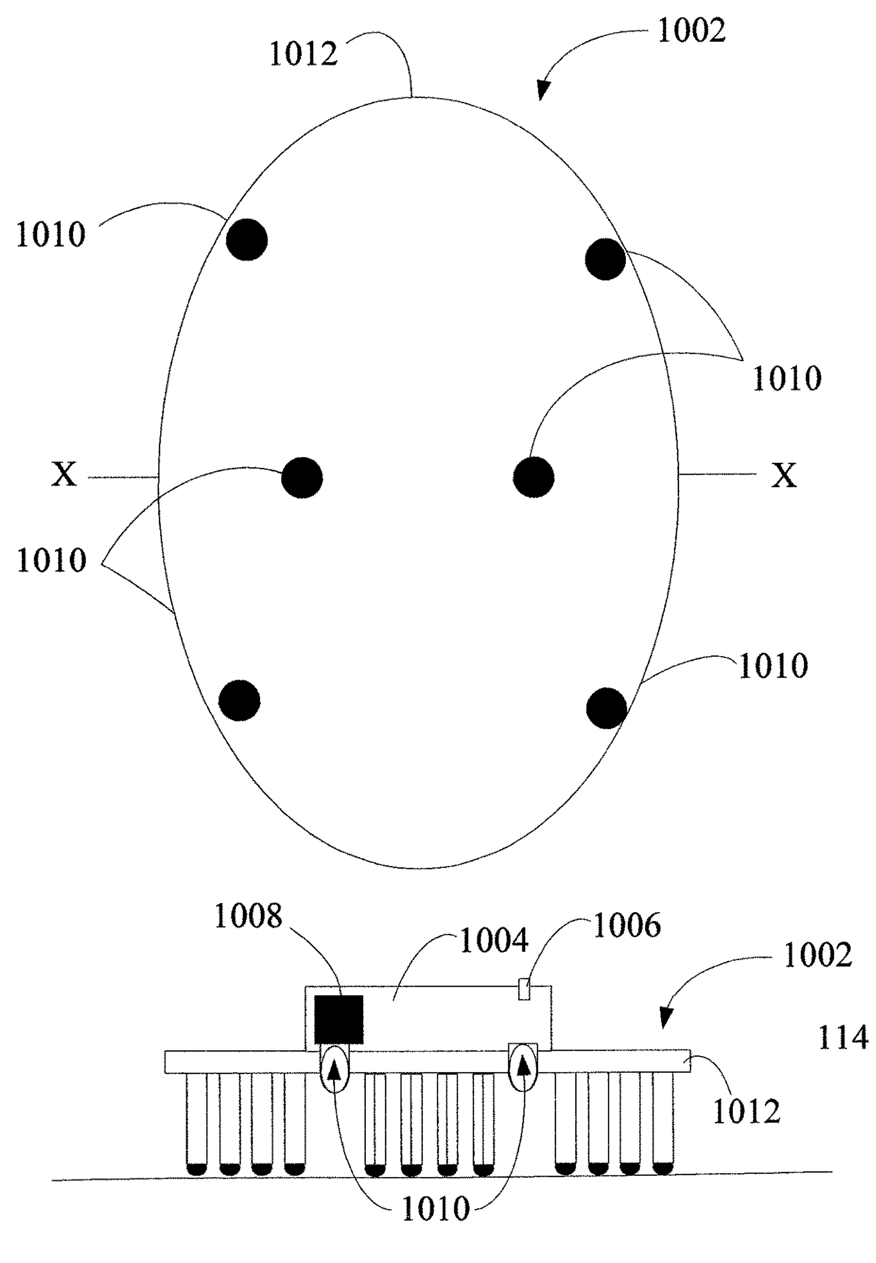
FIG. 10 is a plan view and cross-section view simplified illustration of still another exemplary embodiment in accordance with the current method and apparatus.

Reference is now made to FIG. 10, which is a plan view and cross-section view simplified illustration of head 1002, similar to head 102 of FIG. 1 as viewed in the direction of arrow (W), of another exemplary embodiment in accordance with the current method and apparatus. Head 1002 includes a gel reservoir 1004 that is operative to hold an electric-conductive skin care cleansing gel such as a cleansing soap. Reservoir 1004 may include a refill valve 1006 and dosing pump 1008 communicating with energy source 118 and controller 124 (FIG. 1). Reservoir 1004 dosing pump 1008 may be individually and manually controlled by a dedicated switch (not shown) on handle 104 or by controller 124 (FIG. 1) in accordance with a predetermined protocol.

When activated, dosing pump 1008 may dose a set amount of gel through pores 1010 in carrier 1012 of head 1002.

It will be appreciated by persons skilled in the art that the present invention is not limited to what has been particularly shown and described hereinabove. Rather, the scope of the invention includes both combinations and sub-combinations of various features described hereinabove as well as modifications and variations thereof which would occur to a person skilled in the art upon reading the foregoing description and which are not in the prior art.

What we claim is:

1. An apparatus for cosmetic skin care, the apparatus comprising:

- a head including
  - at least one carrier; and
  - at least two types of bristles arranged in clusters, each including a multiplicity of bristles of the same type attached to the carrier, at least one type of bristles operative to apply forms of energy to the skin wherein at least one of the forms of energy is RF energy;
  - at least one source of energy operative to supply the energy applying bristles; and
- a handle attached to the head and including at least one switch to control the source of energy; and
- wherein a shortest distance between the RF energy applying bristles each being from a different cluster closest to each other is more than combined lengths of the RF energy applying bristles to avoid shorting of RF energy applying bristles.

2. The apparatus according to claim 1, wherein the forms of energy are selected from a group including RF energy, light energy, mechanical energy and ultrasound energy.

3. The apparatus according to claim 1, wherein at least one of the head and the handle is operative to include at least one of an energy source, an RF generator, a light source, a controller and an indicator light.

4. The apparatus according to claim 1, wherein the type of bristles is selected from a group of types including inert bristles and energy applying bristles.

5. The apparatus according to claim 1, wherein each of the bristles is semi-rigid or pliable and is attached to the carrier in a cantilever manner.

6. The apparatus according to claim 4, wherein the clusters are regular RF electrodes.

7. The apparatus according to claim 1, wherein the bristles are light energy applying bristles each comprises at least one optical fiber.

8. The apparatus according to claim 1, wherein the bristles are light energy applying bristles each of the bristles comprises a multiplicity of optical fibers.

9. The apparatus according to claim 8, wherein the optical fibers are at least one of slidingly adhered to each other, protected with a pliable coating and protected with a pliable sleeve.

10. The apparatus according to claim 9, wherein the sleeve ends with a protective transparent cover.

11. The apparatus according to claim 1, wherein the bristles apply light energy in at least one light form selected from a group including coherent light, visible light and Infra-Red (IR) light.

12. The apparatus according to claim 1, wherein the RF energy applying bristle is at least partially electrically isolated.

13. The apparatus according to claim 1, wherein the at least two types of bristles attached to the carrier are operative to apply at least two different forms of energy to the skin.

14. The apparatus according to claim 1, wherein the head also includes at least one LED connected to the carrier.

15. The apparatus according to claim 1, wherein the head also includes at least one soft pad lined with a material easily charged with a stationary electrical charge and operative to collect loose electrically charged skin debris.

16. The apparatus according to claim 1, wherein the carrier also comprises:

- a recess;
- one or more Light Emitting Diodes (LEDs) embedded within the recess;
- a clear plate attached to the carrier covering the recess and forming a transparent window; and
- bristles made of a clear material attached to the clear plate.

17. The apparatus according to claim 1, wherein the carrier includes at least one stationary portion and at least one rotatably moveable portion.

18. The apparatus according to claim 17, wherein the rotatably moveable portion includes RF energy applying bristles communicating with the source of energy via a slip ring assembly or brush assembly.

19. The apparatus according to claim 18, wherein the rotatably moveable portion includes RF energy applying bristles in a monopolar configuration and the handle also includes a common electrode.

20. The apparatus according to claim 18, wherein the rotatably moveable portion includes RF energy applying bristles in a monopolar configuration and the stationary portion includes a grounding electrode.

21. The apparatus according to claim 1, wherein the head also comprises a vibration effecting motor.

22. The apparatus according to claim 1, wherein the head also comprises a piezoelectric element effecting vibration or translational movement.

23. The apparatus according to claim 1, wherein the head also comprises:

a recess including at least one rail on at least one wall thereof;

at least one chassis having at least one wheel supported by and operative to rotate along the rail;

at least one moveable portion of the carrier suspended from the chassis; and at least one electric motor electrically supplied by the energy source and controlled by a controller attached to the wheel.

24. The apparatus according to claim 1, wherein the head also comprises:

a recess including at least one rail on at least one wall thereof and at least one electromagnet having alternating polarity;

at least one chassis having at least one wheel supported by and operative to rotate along the rail; and at least one moveable portion of the carrier suspended from the chassis and having a magnet on at least one margin opposite the electromagnet.

25. The apparatus according to claim 1, wherein the head also comprises:

a gel reservoir operative to hold an electric-conductive gel including:

at least one reservoir refill valve; and at least one dosing pump communicating with the energy source and the controller; and at least one pore in the carrier communicating with the gel reservoir.

26. The apparatus according to claim 1, wherein the forms of energy are applied in at least one of concurrently, consecutively and a combination thereof, and wherein the light energy is applied through light delivering bristles and RF energy is applied through RF energy applying bristles.

* * * * *